(12) United States Patent
Nagase et al.

(10) Patent No.: US 10,962,513 B2
(45) Date of Patent: Mar. 30, 2021

(54) CONCENTRATION DETECTION METHOD AND PRESSURE-TYPE FLOW RATE CONTROL DEVICE

(71) Applicant: FUJIKIN INCORPORATED, Osaka (JP)

(72) Inventors: Masaaki Nagase, Osaka (JP); Kenji Aikawa, Osaka (JP); Kaoru Hirata, Osaka (JP); Takahiro Imai, Osaka (JP); Tetsuo Naritomi, Osaka (JP); Tsutomu Shinohara, Osaka (JP); Takahiro Matsuda, Osaka (JP); Kouji Nishino, Osaka (JP)

(73) Assignee: FUJIKIN INCORPORATED, Osaka (JP)

( * ) Notice: Subject to any disclaimer, the term of this patent is extended or adjusted under 35 U.S.C. 154(b) by 236 days.

(21) Appl. No.: 16/334,848

(22) PCT Filed: Sep. 27, 2017

(86) PCT No.: PCT/JP2017/034956
§ 371 (c)(1),
(2) Date: Mar. 20, 2019

(87) PCT Pub. No.: WO2018/062270
PCT Pub. Date: Apr. 5, 2018

(65) Prior Publication Data
US 2020/0018736 A1    Jan. 16, 2020

(30) Foreign Application Priority Data
Sep. 28, 2016   (JP) .............................. JP2016-189986

(51) Int. Cl.
*G01F 1/36*         (2006.01)
*G01N 9/26*         (2006.01)
(Continued)

(52) U.S. Cl.
CPC ........... *G01N 33/0027* (2013.01); *G01F 1/36* (2013.01); *G01N 9/26* (2013.01); *G05D 7/0635* (2013.01)

(58) Field of Classification Search
CPC ........ G01N 33/0027; G01N 9/26; G01F 1/36; G05D 7/0635
See application file for complete search history.

(56) References Cited

U.S. PATENT DOCUMENTS 4,455,861 A    6/1984   Alftine
4,934,178 A *  6/1990   Jones .................... G01N 9/266
                                                  73/32 R
(Continued)

FOREIGN PATENT DOCUMENTS

JP     2004138425 A    5/2004
JP     2004199109 A    7/2004
(Continued)

OTHER PUBLICATIONS

International Search Report issued in PCT/JP2017/034956; dated Jan. 9, 2018.

*Primary Examiner* — Suman K Nath
(74) *Attorney, Agent, or Firm* — Studebaker & Brackett PC

(57) ABSTRACT

A method for detecting the concentration of a specified gas contained in a mixed gas includes, in a pressure-type flow rate control device including a restriction portion, an upstream valve provided upstream of the restriction portion, and a pressure sensor for measuring the pressure between the restriction portion and the upstream valve, a step of flowing the mixed gas from the upstream side of the upstream valve in a state in which the pressure on the downstream side of the restriction portion is lower than the pressure on the upstream side of the restriction portion, a step of determining with a pressure sensor pressure drop (Continued)

characteristics occurring after the upstream valve is changed from an open to a closed state, and a step of determining the concentration of the specified gas in the mixed gas based on the pressure drop characteristics.

8 Claims, 5 Drawing Sheets

(51) Int. Cl.
  *G01N 33/00* (2006.01)
  *G05D 7/06* (2006.01)

(56) References Cited

U.S. PATENT DOCUMENTS

| | | | |
|---|---|---|---|
| 5,708,190 A * | 1/1998 | Seefeldt | G01L 19/12 |
| | | | 73/23.2 |
| 9,010,174 B2 * | 4/2015 | Lazik | G01N 7/10 |
| | | | 73/31.04 |
| 2009/0326719 A1 | 12/2009 | Nagase et al. | |
| 2012/0006487 A1 | 1/2012 | Kikuchi et al. | |
| 2012/0186564 A1 * | 7/2012 | Vigild | F02D 21/08 |
| | | | 123/559.1 |

FOREIGN PATENT DOCUMENTS

| | | |
|---|---|---|
| JP | 2007-95042 A | 4/2007 |
| WO | 2010113576 A1 | 10/2010 |

\* cited by examiner

CONCENTRATION DETECTION METHOD AND PRESSURE-TYPE FLOW RATE CONTROL DEVICE

TECHNICAL FIELD

The present invention relates to a method for detecting the concentration of a specified gas in a mixed gas using a pressure-type flow rate control device used in semiconductor manufacturing facilities, chemical plants or the like.

BACKGROUND ART

Conventional pressure-type flow rate control devices are known (for example. Patent Document 1, etc.) that include a flow path through which a fluid passes, a restriction portion, such as an orifice plate interposed in the flow path, an upstream pressure sensor for detecting a pressure $P_1$ upstream of the restriction portion, a downstream pressure sensor for detecting a pressure $P_2$ downstream of the restriction portion, a temperature sensor for detecting a temperature T upstream of the restriction portion, a control valve provided upstream of the upstream pressure sensor, and a controller for regulating the control valve. Downstream of such pressure-type flow rate control devices are connected shutoff valves, semiconductor manufacturing device process chambers, vacuum pumps, etc.

Such a pressure-type flow rate control device controls the flow rate by regulating the control valve according to the upstream pressure $P_1$, or the upstream pressure $P_1$ and downstream pressure $P_2$, utilizing the relationship that holds between an upstream pressure $P_1$ detected by the upstream pressure detector, a downstream pressure $P_2$ detected by the downstream pressure detector, and a flow rate Q of the fluid passing through the restriction portion.

Explained more specifically, under critical expansion conditions, that is, under a condition that $P_1 \geq$ about $2 \times P_2$ is satisfied (in the case of argon gas), the relationship between the flow rate $Q=K_1 P_1$ is established, where $K_1$ is a proportional coefficient that depends on the type of fluid and fluid temperature. Under noncritical expansion conditions, the relationship between flow rate $Q=K_2 P_2^m (P_1-P_2)^n$ is established, where $K_2$ is a proportional coefficient depending on the type of fluid and fluid temperature, and indices in and n are values derived from the actual flow rate. In such a pressure-type flow rate control device, the flow rate can be calculated from the output of the pressure sensor using these flow rate calculation equations, and the degree of opening/closing the control valve is regulated so that the obtained flow rate can equal the set flow rate.

PRIOR ART DOCUMENTS

Patent Documents

[Patent document 1] Japanese Unexamined Patent Publication No. 2004-138425

[Patent document 2] International Patent Publication No. 2010/113576

[Patent document 3] Japanese Unexamined Patent Publication No. 2007-95042

[Patent document 4] Japanese Unexamined Patent Publication No. 2004-199109

SUMMARY OF INVENTION

Problems to be Solved by Invention

When using such an above-described pressure-type flow rate control device, a mixed gas of a source gas and a diluent gas (or carrier gas) can be regulated to have a desired flow rate prior to be supplied to a process chamber. For example, in MOCVD (metalorganic chemical vapor deposition), in some cases an organometallic material vapor is admixed with a carrier gas using a bubbling device or the like to generate a mixed gas, and the mixed gas is supplied to the process chamber at a controlled flow rate. Furthermore, a highly reactive gas, for example, fluorine gas diluted with an inert diluent gas (for example, Ar gas or $N_2$), can be supplied to the process chamber as a mixed gas. A gas cylinder filled with a mixed gas obtained by diluting fluorine gas to about 20% is sometimes used as a mixed-gas supply source. In addition, in conventional semiconductor manufacturing processes, various source gases are mixed with a diluent gas or a carrier gas; the flow rate is controlled by a pressure-type flow rate control device; and the resulting gas mixture is supplied to the process chamber as a mixed gas.

Particularly, in recent years, precise control of the concentration of the source gas in the mixed gas supplied to the process chamber has been required. Patent document 2 describes a configuration in which a diluent gas supply line valve is adjusted according to the measured fluorine gas concentration in a fluorine gas supply system using a UV-visible spectrophotometer as a concentration measuring device. By directly measuring the concentration of the source gas using the concentration measuring device, it is possible to accurately control the concentration of the source gas.

However, when a concentration measuring device is provided in a mixed gas supply system as described in Patent document 2, there is the problem that it inevitably increases the size and cost of the apparatus.

The present invention has been made in view of the above problem, and its main object is to provide a method for concentration detection in a pressure-type flow rate control device without a separately-provided concentration measuring device.

Solution to Problem

A method for detecting a concentration according to one embodiment of the present invention is a method for detecting the concentration of a specified gas contained in a mixed gas, the method comprising: in pressure-type flow rate control device comprising a restriction portion, an upstream valve provided upstream of the restriction portion, and a pressure sensor for measuring the pressure between the restriction portion and upstream valve, including a step of flowing the mixed gas from upstream of the upstream valve in a state that the pressure on the downstream side of the restriction portion is lower than that on the upstream side of the restriction portion; a step of detecting, by the pressure sensor, one or more pressure drop characteristics occurring after the upstream valve is changed from open to closed; and a step of detecting the concentration of the predetermined gas in the mixed gas based on the detected one or more pressure drop characteristics.

In one embodiment, the step of detecting the concentration of the specified gas includes a step of storing pressure drop characteristics detected when the specified gas has a predetermined concentration as reference pressure drop characteristics in a storage device, and a step of detecting the concentration of the specified gas by comparing the detected pressure drop characteristics with the reference pressure drop characteristics stored in the storage device.

In one embodiment, the pressure drop characteristics are defined by the time required for the pressure indicated by the pressure sensor to drop to a specified pressure after changing the upstream valve to a closed state.

In one embodiment, the pressure drop characteristics are defined by the pressure reached after a specified time has elapsed after changing the upstream valve to a closed state.

In one embodiment, the pressure drop characteristics are detected under the conditions satisfying critical expansion conditions.

In one embodiment, the mixed gas includes a diluent gas and a source gas, and detects the concentration of the source gas as the specified gas.

In one embodiment, the upstream valve is a control valve for regulating the flow rate of the mixed gas.

A pressure-type flow rate control device according to one embodiment of the present invention includes a restriction portion, an upstream valve provided upstream of the restriction portion, a pressure sensor for measuring a gas pressure between the restriction portion and the upstream valve, and a controller that receives an output of the pressure sensor, the pressure-type flow rate control device being configured to allow a mixed gas to flow from upstream of the upstream valve, so that the controller determines pressure drop characteristics occurring after the upstream valve is changed from an open to a closed state according to output from the pressure sensor, and determines the concentration of the predetermined gas in the mixed gas based on the pressure drop characteristics.

Effects of Invention

According to embodiments of the present invention, it is possible to detect the concentration of a source gas in a mixed gas by using a pressure-type flow rate control device without providing a separate concentration measuring device.

MODE FOR CARRYING OUT INVENTION

Figure 1:
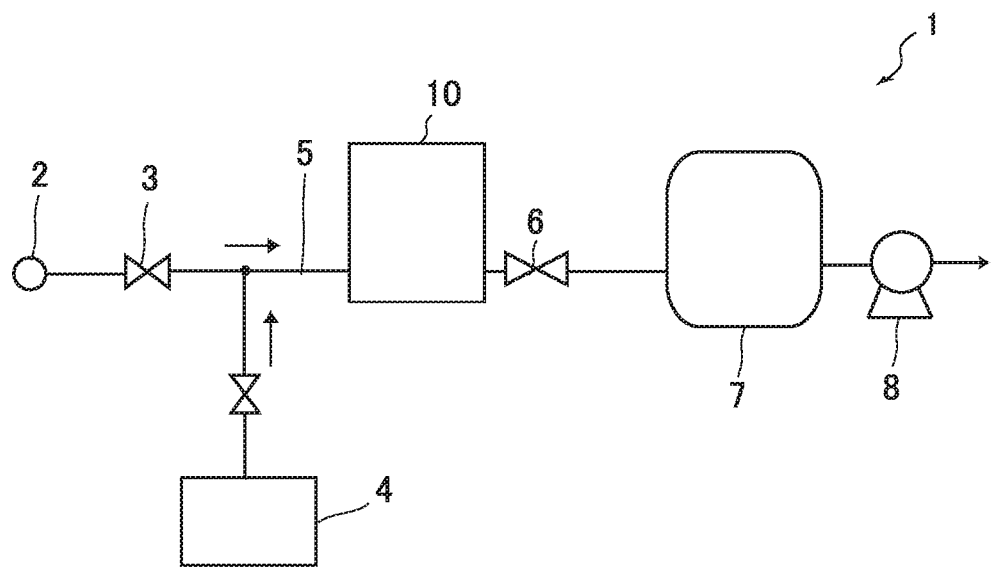
FIG. 1 is a schematic diagram showing an example of a mixed gas supply system provided with a pressure-type flow rate control device according to one embodiment of the present invention.

A pressure-type flow rate control device and a method for detecting a concentration using the same according to embodiments of the present invention will be described below with reference to the drawings, but the present invention is not limited to the following embodiments, FIG. 1 shows an example of a mixed gas supply system 1 incorporating a pressure-type flow rate control device 10 according to this embodiment. The mixed gas supply system 1 includes a flow control valve 3 interposed between a diluent gas supply source 2 and a diluent gas supply line extending from the diluent gas supply source 2, a source gas supply source 4, a mixed gas introduction portion 5 which is in communication with the diluent gas supply source 2 and the source gas supply source 4, a pressure-type flow rate control device 10 provided downstream of the mixed gas introduction portion 5, an on-off valve 6 provided downstream of the pressure-type flow control device 10, a process chamber 7 connected downstream of the on-off valve 6, and a vacuum pump 8 connected to the process chamber 7.

The diluent gas and the source gas are introduced into the pressure-type flow rate control device 10 as a mixed gas via the mixed gas introduction portion 5 configured to join the diluent gas supply line and the source gas supply line. The mixed gas introduction portion 5 may include a mixing block connecting the diluent gas supply line and the source gas supply line, a buffer tank for homogenizing the mixed gas, etc.

The pressure-type flow rate control device 10 controls the flow rate of the mixed gas introduced from the mixed gas introduction unit 5 and supplies it to the process chamber 7. The inside of the process chamber 7 can be evacuated by the vacuum pump 8, and the mixed gas is supplied to the process chamber 7 in a state where the downstream side of the pressure-type flow rate control device 10 is depressurized.

The mixed gas supply system 1 may take any mode as long as it is a system configured to supply a mixed gas while controlling the flow rate using a pressure-type flow rate control device. For example, in the embodiment exemplified above, the flow control valve 3 is provided in the diluent gas supply line, but it is also possible to provide a flow rate control device (for example, a thermal mass flow controller) in both the diluent gas supply line and the source gas supply line. Furthermore, the diluent gas and the source gas may be stored in a gas tank or the like in advance as a mixed gas. In addition, for MOCVD a system may be used in which a mixed gas produced by adding a source gas vapor into a carrier gas with a bubbling device is supplied to a process chamber via a pressure-type flow rate control device, or a system in which a solid material is sublimed into a diluent gas so that a source gas is added to the diluent gas, and the resulting gas is supplied as a mixed gas. Furthermore, a supply system for not only a two-component gas mixed gas but also a three- or more-component gas may instead be employed.

Examples of source gases include oxygen, fluorine, germane, diborane, etc. Examples of diluent (carrier) gases include argon, nitrogen, helium, hydrogen, etc. The source gas may be a material gas for depositing a thin film, or a gas used as an etching gas. Examples of the combination of "source gas/diluent gas" in the mixed gas include $O_2$/He, $PH_3$/$H_2$, $GeH_4$/$H_2$, $B_2H_6$/$H_2$, etc.

If desired, the concentration of the source gas in the mixed gas can be set, for example, by adjusting the opening/closing degree of the flow rate control valve 3. In the case where flow rate control devices are provided in both the diluent gas supply line and the source gas supply line, it is possible to adjust the concentration of the source gas by controlling the flow ratio between the diluent gas and the source gas.

Figure 2:
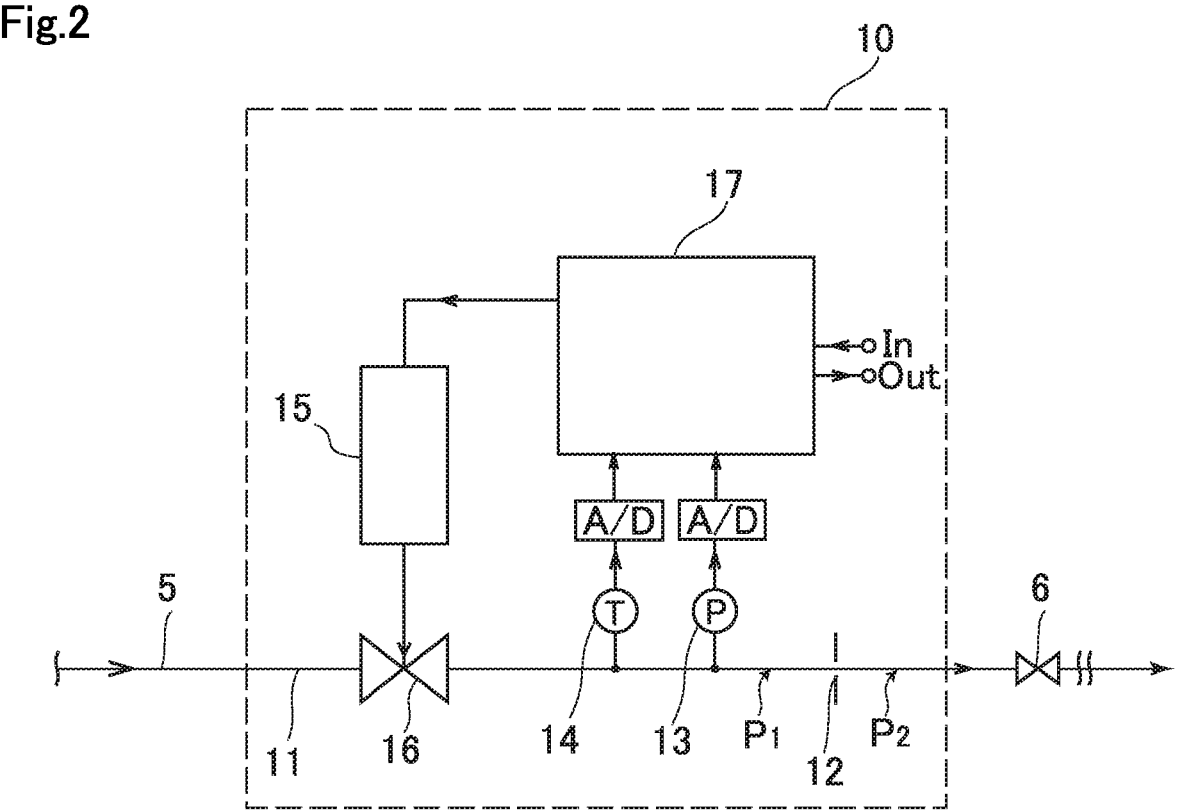
FIG. 2 is a schematic diagram showing the configuration of a pressure-type flow rate control device according to one embodiment of the present invention.

The configuration of a pressure-type flow rate control device 10 according to the present embodiment will be described below with reference to FIG. 2. The pressure-type flow rate control device 10 includes a restriction portion 12 interposed in the flow path 11, a control valve 16 interposed in the flow path 11 upstream of the restriction portion 12, an upstream pressure sensor for detecting a pressure $P_1$ upstream of the restriction portion 12 between the restriction portion 12 and the control valve 16, a temperature sensor 14 for detecting the temperature between the restriction section 12 and the control valve 16, and a control board 17 provided with a controller (arithmetic control unit).

The pressure-type flow rate control device 10 may further include a downstream pressure sensor (not shown) for detecting a pressure $P_2$ downstream of the restriction portion 12. Furthermore, an on-off valve 6 as shown in FIG. 1 may be incorporated in the pressure-type flow rate control device 10. A critical flow nozzle or a sonic nozzle may be used instead of the orifice member as the restriction portion 12. The diameter of the orifice or nozzle may be adjusted to, for example, 10 μm to 500 μm. Valves incorporating an orifice having an orifice member such as an orifice plate in the vicinity of the on-off valve are known, and can be used as an integrated unit for the restriction portion 12 and the on-off valve 6.

In the present embodiment, the opening and closing operation of the on-off valve 6 is regulated by an external control device (not shown) connected to a control board 17 provided with the controller, but in another embodiment, it may be regulated by the controller. A standard fluid operated valve (air-operated valve or the like), for example, whose supply of compressed air is controlled by a solenoid valve, can be used as the on-off valve 6.

The flow path 11 of the pressure-type flow rate control device 10 may be constituted by piping, or it may be constituted by flow path holes formed in a metallic block. The upstream pressure sensor 13 may contain, for example, a silicon single crystal sensor chip and a diaphragm. The control valve 16 may be, for example, a piezoelectric element drive-type control valve that opens and closes a metallic diaphragm valve using a drive unit 15 configured by a piezo element (piezo actuator).

In the pressure-type flow rate control device 10, the controller provided with the control board 17 controls the control valve 16 so that the flow rate passing through the restriction portion 12 becomes the set flow rate according to the detection outputs from the upstream pressure sensor 13 and the temperature sensor 14. The controller includes a CPU, a memory (storage device) M such as ROM or RAM, an A/D converter, etc. The controller may include a computer program configured to perform the operations described below and may be realized by a combination of hardware and software. Note that the A/D converter shown in FIG. 2 may be provided on the control board 17 or may be incorporated into a processor mounted on the control board 17.

In the controller, the CPU executes a program stored in the ROM, thereby realizing the function of the pressure-type flow rate control device. The controller (or the control board 17) may be provided with an interface for exchanging information with an external device such as a computer, so that it is possible to write programs and data from the external device to the ROM. It is not necessary that all of the constituent elements (CPU, etc.) of the controller are integrally provided in the device, and some constituent elements such as the CPU may be arranged in different locations (outside the apparatus) and be mutually connected by buses. In such a case, the inside and outside of the device may be configured to allow for not only wired communication but also for wireless communication.

In a semiconductor manufacturing process, when supplying a gas to the process chamber 7, the controller determines the flow rate by calculation using at least the output of the upstream pressure sensor 13, and regulates the control valve 16 (specifically, the driving unit 15) so that the flow rate passing through the restriction portion 12 equals the set flow rate. The flow rate obtained by the calculation may be displayed as the flow rate output value on a display unit of an external control device. The flow rate control may be performed by conventional methods (for example, the method described in Patent document 1). For instance, when critical expansion conditions ($P_1 \geq$ about $2 \times P_2$, in the case of argon gas) are satisfied, the flow rate Q can be controlled by the flow rate $Q=K_1 P_1$ (where $K_1$ is a proportional coefficient depending on the type of fluid and fluid temperature), and feedback control may be performed on the control valve 16 so that the calculated flow rate becomes equal to the set flow rate.

The pressure-type flow rate control device 10 in the present embodiment can determine the concentration of the specified gas in a mixed gas on the basis of the pressure drop characteristics generated when the control valve 16 is changed from the open state to the closed state. Hereinafter, a specific method for detecting the concentration will be described with reference to FIG. 3.

Figure 3:
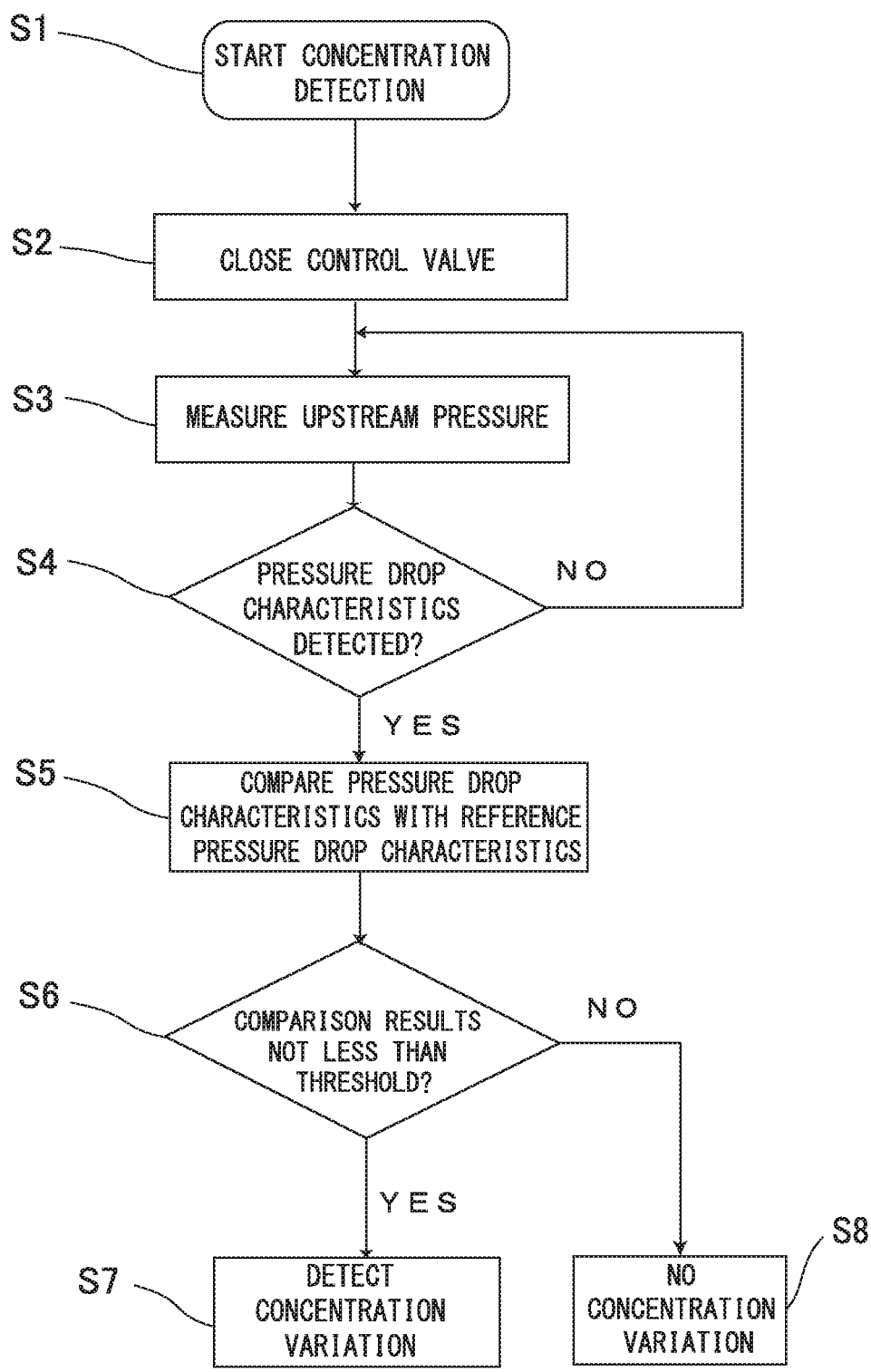
FIG. 3 is a flowchart showing a method for detecting a concentration using a pressure-type flow rate control device according to one embodiment of the present invention.

First, as shown in step S1 of FIG. 3, the procedure of concentration detection is started. The concentration detection is started, for example, in a state where the control valve 16 and the on-off valve 6 are fully opened, that is, a state in which the mixed gas is supplied to the process chamber 7 at a 100% flow rate. At this time, the downstream side of the on-off valve 6 is depressurized by the vacuum pump 8 connected to the process chamber 7. However, the present invention is not limited to this, and the procedure of the concentration detection may be started from a state in which the mixed gas is flowing at a given flow rate setting upon the completion of one process of a semiconductor manufacturing process (for example, a state in which the mixed gas is flowing at a flow rate of 60%).

Next, as shown in steps S2 and S3, the control valve 16 is closed and the drop of the upstream pressure $P_1$ is measured by using the upstream pressure sensor 13. The operation of closing the control valve 16 can be performed, for example, by inputting a signal to set the set flow rate to zero.

Since the pressure $P_2$ on the downstream side of the orifice is lower than the pressure $P_1$ on the upstream side of the orifice, the upstream pressure $P_1$ drops after closing the control valve 16. During this process, the on-off valve 6 may be maintained in an open state or may be shifted to a closed state. If the on-off valve 6 is left in the open state, the pressure of the upstream pressure $P_1$ drops so as to approach the pressure in the process chamber 7. However, when the on-off valve 6 is closed at the same time as closing the control valve 16 or after closing the control valve 16, the upstream pressure $P_1$ drops and the downstream pressure $P_2$ rises, both changing towards an equilibrium pressure P'. When closing the on-off valve 6, there is the advantage that that gas supply to the process chamber can be quickly and reliably stopped.

In the present embodiment, the drop in the upstream pressure $P_1$ caused by closing the control valve 16 is measured, but the present invention is not limited to this. A pressure drop may be caused by closing an on-off valve (not shown) or the like provided upstream of the control valve 16. In this specification, an optional flow path-blocking mechanism provided upstream side of the restriction portion 12 may be referred to as an upstream valve (including control valve 16).

The pressure drop characteristics can be defined, for example, by a pressure drop curve indicating the drop in the upstream pressure with respect to time. In order to obtain this pressure drop curve, the upstream pressure $P_2$ may be measured with the upstream pressure sensor 13 until pressure drop characteristics are detected at a specified sampling rate as shown in step S4.

Herein, the pressure drop characteristics is preferably detected in a period satisfying critical expansion conditions. For this reason, the device may be configured so that the downstream pressure $P_2$ is measured using the downstream pressure sensor, and it is determined whether or not the upstream pressure $P_1$ measured to obtain the pressure drop characteristics is obtained when the critical expansion condition is satisfied is determined. Furthermore, when the range of upstream pressures satisfying critical expansion conditions can be inferred in advance, only upstream pressures within the predetermined pressure range may be used for detecting the pressure drop characteristics.

The minimum pressure ratio $P_1/P_2$ which can satisfy critical expansion conditions varies depending on the type of gas. For example, it is 2.05 in the case of argon gas, but there is a particular value for each gas type, such as 1.90 for hydrogen and 1.89 for nitrogen. In addition, the critical expansion conditions also vary with the upstream gas temperature. Therefore, the controller may be configured to determine a conditional expression for determining whether or not it is under critical expansion conditions based on at least one of the type of gas and the upstream gas temperature.

Next, in step S4, when a predetermined pressure drop characteristics can be detected, in step S5, the characteristic of the measured pressure drop and the reference pressure drop characteristics previously stored in the storage device (memory M) of the controller are compared.

Herein, the reference pressure drop characteristics are pressure drop characteristics determined when a specified gas (a gas whose concentration is to be determined) in the mixed gas is at a particular concentration, and are associated with a predetermined concentration (for example, 20%) to be stored in the storage device as reference pressure drop characteristics. The reference pressure drop characteristics may be obtained in advance in a state in which it is confirmed that the concentration is stable, for example. However, the reference pressure drop characteristics are not limited to these, and may be pressure drop characteristics from a previous measurement or even predetermined pressure drop characteristics not depending on measurement.

Comparison of the measured pressure drop characteristics with the reference pressure drop characteristics which are read from the storage device may be done in various ways. The pressure drop characteristics may be defined, for example, by the time required for the pressure $P_1$ indicated by the upstream pressure sensor to drop to a specified pressure after changing the control valve to the closed state. In this case, the reference pressure drop characteristics are also recorded as the time required to drop to the same predetermined pressure, and by comparing these times, it is possible to detect any variation in concentration from the predetermined concentration. Alternatively, the pressure drop characteristics may be defined by the pressure reached after elapse of a specified time after changing the control valve to the closed state. In this case the reference pressure drop characteristics are recorded as the pressure to be reached, and it is possible to detect variation from a specified concentration by comparing these.

Furthermore, concentration detection using the pressure drop characteristics may be performed by comparing a plurality of pressure drop data obtained by sampling with a corresponding plurality of reference pressure drop data stored in advance.

For example, the value $\ln(P_{(t)}/P_0)$ which is the logarithmic value obtained after dividing the pressure drop data $P_{(t)}$ by the initial pressure $P_0$ can be represented as $\ln(P_{(t)}/P_0)=SC(RT)^{1/2}/V \cdot t$. Here, S is the opening cross-sectional area; C is a constant depending on the gas; R is the gas constant; T is the upstream gas temperature; and V is the flow path volume between the control valve and restriction portion. Assuming that C, R, T, and V are constants that are not dependent on time, it can be represented that $\ln(P_{(t)}/P_0)=-\alpha t$ (where $\alpha$ is a constant), and therefore $\ln(P_{(t)}/P_0)$ can be defined as a linear function for time t. For this reason, the gradient $\alpha$ of the approximately straight line determined according to $\ln(P_{(t)}/P_0)$ obtained by measurement (for example, the approximately straight line obtained by least squares method using all or part of the sample data determined to satisfy critical expansion conditions may be compared with a reference gradient $\alpha$ stored in the memory M in advance as reference pressure drop data to detect any variation in concentration based on the results.

When the concentration of the specified gas in the mixed gas changes, C and R in the above formula change. As a result, $\ln(P_{(t)}/P_0)$ and gradient $\alpha$ change according to the change in concentration. For this reason, it is possible to detect changes in concentration by comparing these with the reference data.

Thus, when comparing with the reference pressure drop characteristics, as shown in step S6, when the comparison result is equal to or greater than the threshold value, a change in concentration can be detected as shown in step S7. Furthermore, the concentration after the change can be determined according to the magnitude of the change of the measured pressure drop characteristics with respect to the reference pressure drop characteristics. This is a method realized based on the knowledge of the present inventors that the magnitude of the change in the concentration of a specified gas in a mixed gas is reflected in the magnitude of the change in the pressure drop characteristics in the pressure-type flow rate control device. As will be described later with reference to FIG. 6, the concentration of the source gas in the mixed gas and the pressure drop characteristics have a characteristic relationship, and therefore it is possible to estimate the concentration of the source gas from the detected pressure drop characteristics.

If it is determined in step S6 that the comparison result is less than the threshold value, no significant concentration change has occurred as shown in step S8, and it can be therefore determined that the specified concentration associated with the reference pressure drop characteristics is maintained.

In addition, the controller is configured to be capable of executing a self-diagnosis function at the time of terminating a semiconductor manufacturing device process (at the time of stopping gas supply to the process chamber) and in a maintenance mode. One known self-diagnosis method uses pressure drop characteristics when the control valve is changed from the open state to the closed state (for example, Patent document 3). The pressure-type flow rate control device 10 of the present embodiment may also have a self-diagnosis function, so that the pressure drop characteristics can be measured using this self-diagnosis function and the measured pressure drop characteristics compared with the reference pressure drop characteristics to allow concentration determination.

While the method for detecting a concentration described above can be applied to various mixed gases, it can be preferably performed on a mixed gas containing different kinds of gases whose flow factors differ greatly in particular. The reason will be explained below. Usually, source gases and diluent gases have different flow factors. Herein, "flow factor" is an index indicating the relationship between gas pressure and the degree of ease of flow, which varies depending on the type of fluid (for example, Patent document 4).

For example, in the case where a source gas having a smaller flow factor than the diluent gas is contained in a mixed gas, if the concentration of the source gas decreases, the pressure drop curve shifts downward (that is, the pressure drop is more likely to occur). In addition, the larger the difference in flow factor between the source gas and the diluent gas, the greater the pressure drop curve changes due to the change in concentration of the source gas. Therefore, the amount of change in the concentration change can be estimated from the amount of change in the pressure drop curve in consideration of the difference and flow factor ratio. When the flow factor of nitrogen is 1, the relative flow factor is, for example, Ar=about 0.887, He=about 2.81, $H_2$=about 3.74, $O_2$=about 0.935, $N_2O$=about 0.765, $NH_3$=1.236, and are thus different depending on the type of gas.

A specific example of the relationship between the source gas concentration in the mixed gas and the pressure drop characteristics will be described below.

Figure 4:
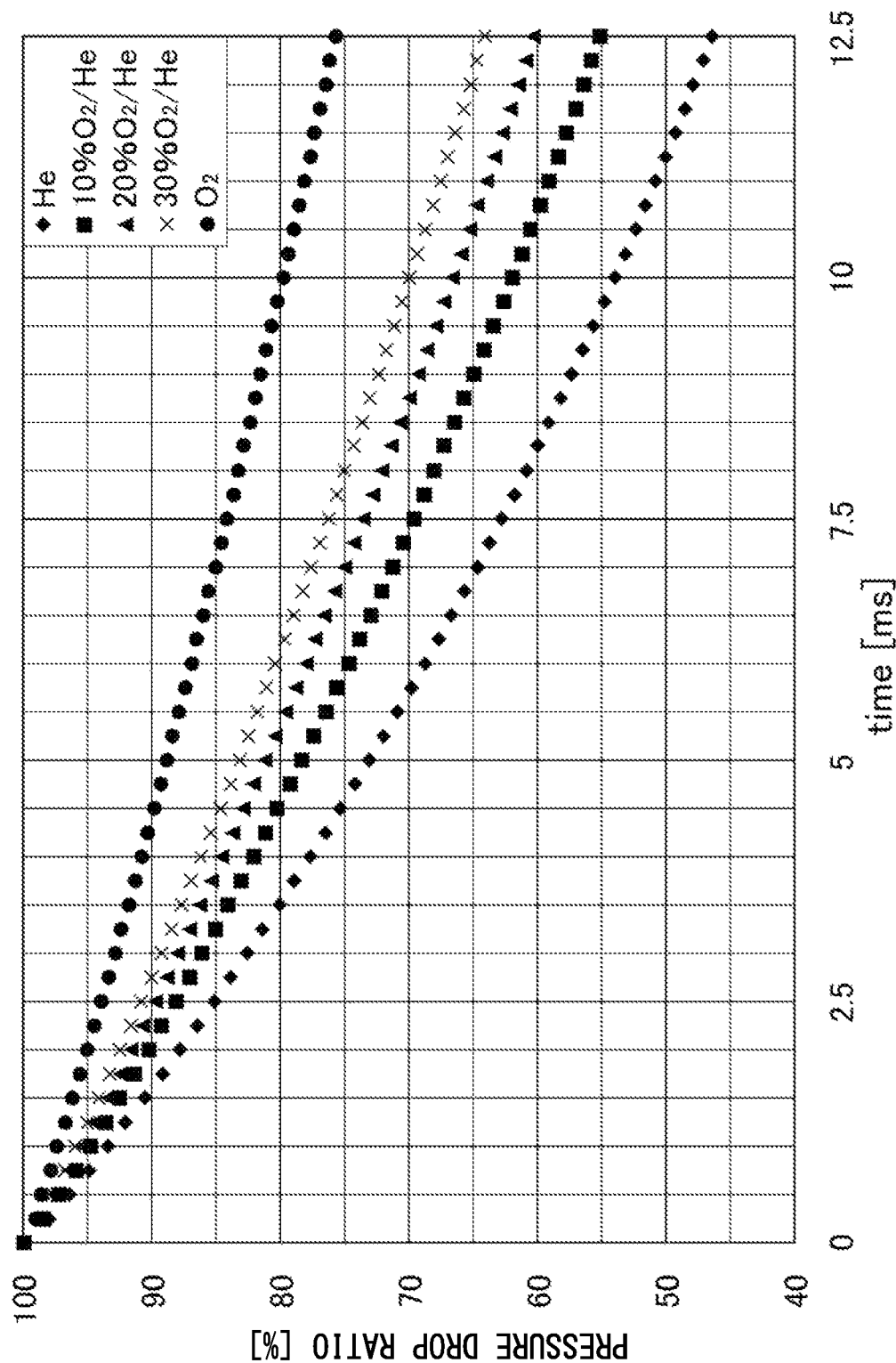
FIG. 4 is a graph showing how pressure drop characteristics vary with the concentration of a specified gas in a mixed gas.
Figure 5:
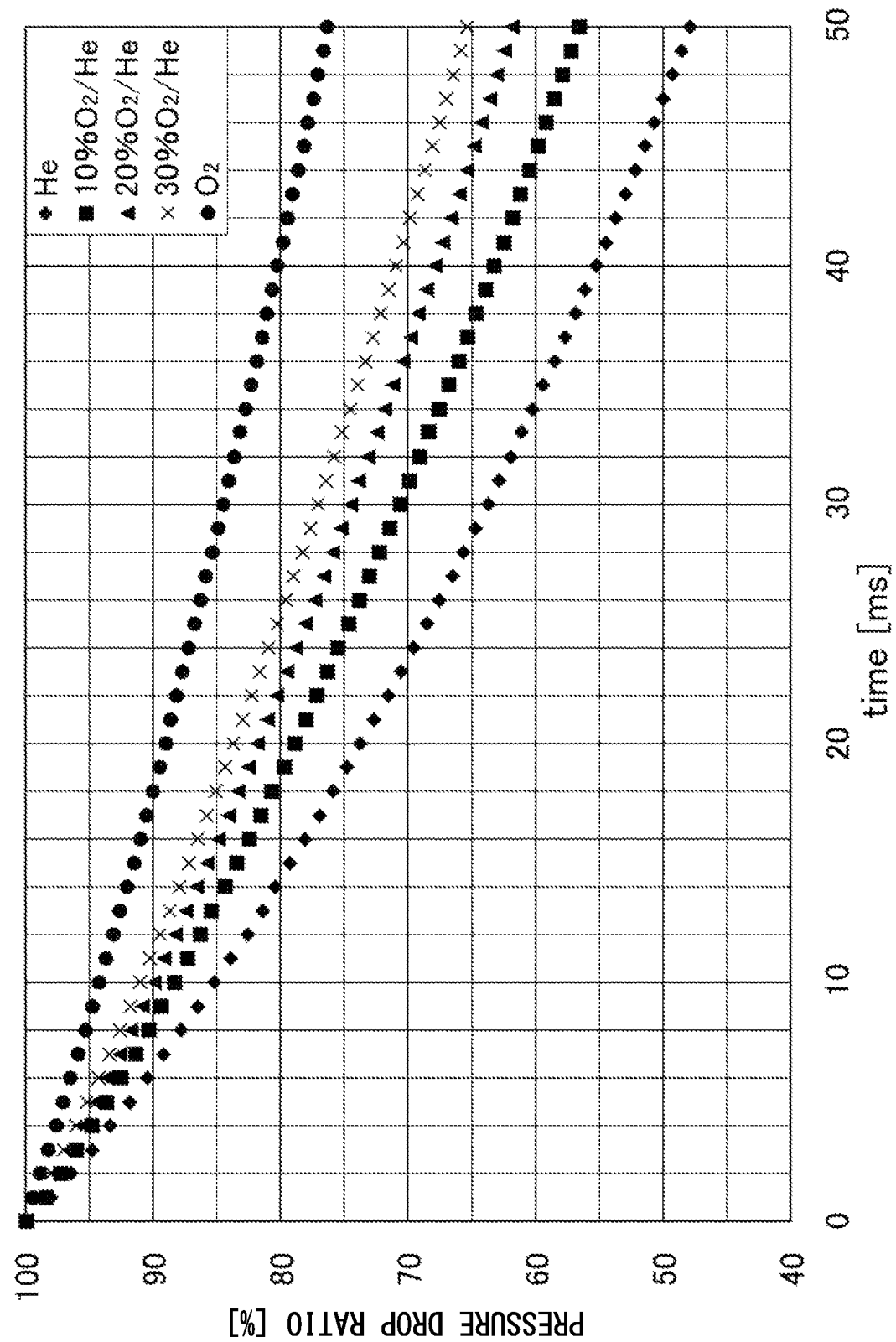
FIG. 5 is a graph showing how pressure drop characteristics vary with the concentration of a specified gas in a mixed gas.

FIGS. 4 and 5 are graphs showing the difference in pressure drop characteristics occurring depending on the concentration of the source gas in the mixed gas. FIG. 4 shows a case where the flow rate range is a relatively small flow rate (F160), while FIG. 5 shows a case where the flow rate range is a relatively large flow rate (F300). The graphs shown in FIG. 4 and FIG. 5 show the pressure drop characteristics in the case of 100% helium (He), the $O_2$ concentration in the mixed gas of helium and oxygen: 10% (10% $O_2$/He), the $O_2$ concentration in the mixed gas of helium and oxygen: 20% (20% $O_2$/He), the $O_2$ concentration in the mixed gas of helium and oxygen: 30% (30% $O_2$/He), and 100% oxygen ($O_2$). The horizontal axis shows the time elapsed after the upstream valve is closed, while the vertical axis shows the upstream pressure as a pressure drop ratio (%) relative to the upstream pressure (initial pressure) at the time of closing the upstream valve (time 0) being 100%.

As can be seen from FIGS. 4 and 5, the pressure drop characteristics change as the oxygen concentration in the helium-oxygen mixed gas decreases and the pressure drop per hour per unit time increases as the oxygen concentration decreases. Therefore, by measuring the pressure drop characteristics (for example, the time until the pressure drop ratio reaches 70%), it is possible to obtain changes in the oxygen concentration in the mixed gas and an estimated concentration. In addition, it can be seen from the results shown in FIGS. 4 and 5 that as the oxygen concentration in the helium-oxygen mixed gas decreases, the gas more easily flows through the orifice, and the flow factor increases.

Figure 6:
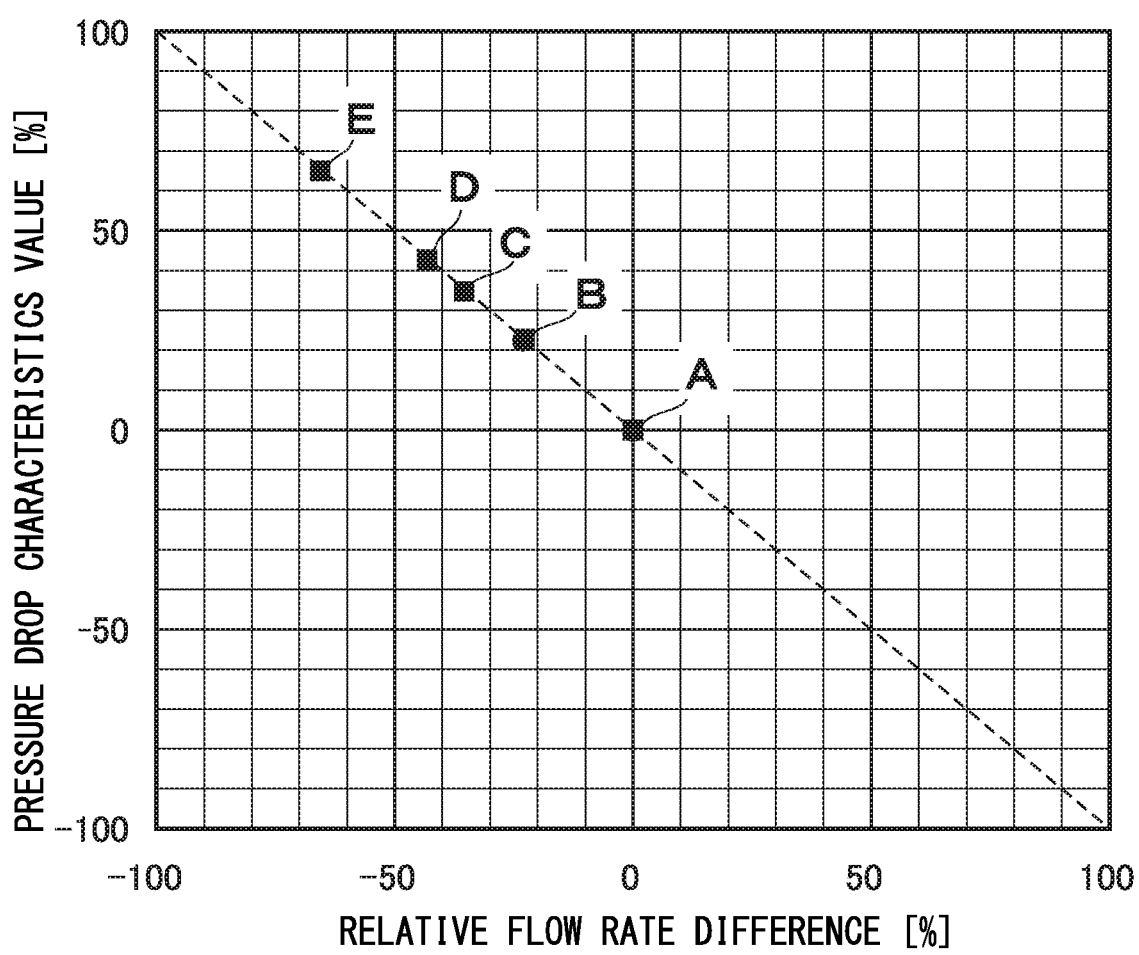
FIG. 6 is a graph showing the relationship between flow rate relative difference and pressure drop characteristics value when a gas of a known concentration is used as a reference.

FIG. 6 is a graph showing the relationship between the relative flow rate difference (horizontal axis) and the pressure drop characteristics value (vertical axis), which is correlated with the concentration of the oxygen gas mixed with the helium gas. In this graph, the case where the oxygen concentration is 0%, that is, when the helium is 100%, is defined as origin A (0, 0); the case where the oxygen concentration is 10% is represented by point B; the case where the oxygen concentration is 20% is represented by point C; the case where the oxygen concentration is 30% is represented by point D; and the case where the oxygen concentration is 100% is represented by point E.

In the graph of FIG. 6, the horizontal axis shows the change in relative flow rate difference with respect to 100% helium with varying concentrations of oxygen gas in the mixed gas at steady state flow rates under critical expansion conditions.

More specifically, the horizontal axis determines the flow factors at the oxygen concentrations (10%, 20%, 30%) based on a flow factor (for $N_2$) of about 2.81 in the case of 100% helium, and a flow factor (for $N_2$) of about 0.94 in the case of 100% oxygen, and shows as the ratio relative to the flow factor (about 2.81) for 100% helium. On the horizontal axis, the oxygen concentration is 0% (helium 100%) at origin A, and the oxygen concentration increases and the flow factor decreases as the relative flow rate difference decreases (that is, towards the left side of the horizontal axis). With an oxygen concentration of 100% at point E, the relative flow rate difference is (1-0.94/2.81)=about -66.7%.

In addition, the vertical axis shows the pressure characteristic value at each point where the oxygen concentration differs with the pressure drop characteristics value at origin A set as a reference. More specifically, the magnitude of the difference between the pressure drop characteristics at each oxygen concentration shown in FIGS. 4 and 5 and the pressure drop characteristics with helium 100% as the reference is shown. In the present embodiment, the pressure drop characteristics value A is Oven by the following equation (1).

[Equation 1]

$$A = \sum \left[ -\frac{1}{\sqrt{T'}} \ln\left(\frac{P'_t}{P'_0}\right) + \frac{1}{\sqrt{T}} \ln\left(\frac{P_t}{P_0}\right) \right] \quad (1)$$

Herein, T', $P'_t$, and $P'_0$ are the temperature, pressure drop data, and initial pressure when the pressure drop characteristics are measured at each oxygen concentration, while T, $P_t$, $P_0$ are the temperature, pressure drop data, and initial pressure in the case of 100% helium. As can be seen from equation (1), in the present embodiment, the pressure drop characteristics values shown in FIG. 6 are determined by using upstream pressure sampling data when the reference helium helium is 100% and upstream pressure sampling data with each oxygen concentration (refer to FIG. 4 and FIG. 5). In FIG. 6, the pressure drop characteristics value is indicated by % in accordance with the flow rate relative difference by standardization.

As can be seen from FIG. 6, on the basis of the pressure drop characteristics value at the specified gas concentration (herein, oxygen concentration: 0%), the relative flow rate difference and the pressure drop characteristics value have linear relationships. Therefore, if a linear equation showing these relationships is obtained in advance, it is possible to estimate the relative flow rate difference, and thus the oxygen concentration, from the pressure drop characteristics values obtained by measurement, even for a mixed gas containing an unknown concentration of oxygen.

Next, a case of using the pressure drop characteristics data in flow rate self-diagnostic measurement when measuring pressure drop characteristics data to detect the concentration of a specified gas in a mixed gas will be described.

As described above, some pressure-type flow rate control devices are equipped with a flow rate self-diagnosis function, and normally, in order to detect clogging of an orifice or the like, a pressure drop characteristic used as a reference in a state where a normal state is confirmed at the time of initial setting is measured, and is compared with pressure drop characteristics measured thereafter. At this time, the measurement at the time of initial setting is performed with helium gas, and flow rate self-diagnosis is performed with a helium/oxygen mixed gas at various concentration ratios, whereby the concentration detection can be performed using the flow rate self-diagnosis results. In addition, it has been found by the inventors of the present invention that, assuming gas A and gas B are different gases, and the initial setting of the flow rate self-diagnosis is performed with gas B and the flow rate self-diagnosis is performed with gas A, the relative flow rate difference of gas A during the reference diagnosis on gas B at the time of flow rate self-diagnosis is equal to the product of the relative difference from the reference value of the flow rate self-diagnosis results and −1. Therefore, pressure drop data for helium gas can be obtained even by using the reference pressure drop data (for example, data of nitrogen gas at the time of initial setting) at the flow rate self-diagnosis of different gas species. As for different mixed gases having different oxygen concentrations, concentration detection can be also performed by comparing the pressure drop data of helium gas as reference data.

INDUSTRIAL APPLICABILITY

The method for determining a concentration according to the embodiment of the present invention can be suitably used for detecting changes in the concentration of a specified gas in a mixed gas using a pressure-type flow rate control device incorporated into a mixed gas supply line used for a semiconductor manufacturing device or the like.

EXPLANATION OF REFERENCE NUMERALS

1 Mixed gas supply system
2 Diluent gas supply source
3 Flow rate control valve
4 Source gas supply source
5 Mixed gas introduction portion
6 On-off valve
7 Process chamber
8 Vacuum pump
10 Pressure-type flow rate control device
11 Flow path
12 Restriction portion
13 Upstream pressure sensor
14 Temperature sensor
15 Driving unit
16 Control valve
17 Control board

The invention claimed is:

1. A method for detecting a concentration of a specified gas contained in a mixed gas, in a pressure-type flow rate control device comprising a restriction portion, an upstream valve provided upstream of the restriction portion, and a pressure sensor for measuring a pressure between the restriction portion and the upstream valve, the method comprising:
a step of flowing the mixed gas from the upstream side of the upstream valve in a state such that the pressure downstream of the restriction portion is lower than the pressure on the upstream side of the restriction portion;
a step of detecting by the pressure sensor pressure drop characteristics occurring after changing the upstream valve from an open to a closed state, and
a step of determining the concentration of the specified gas in the mixed gas on the basis of the pressure drop characteristics.

2. The method for detecting a concentration according to claim 1, wherein the step of detecting the concentration of the predetermined gas comprises:
a step of storing pressure drop characteristics determined when the specified gas has a specified concentration as reference pressure drop characteristics in association with the specified concentration in a storage device, and
a step of determining the concentration of the specified gas by comparing the detected pressure drop characteristics with the reference pressure drop characteristics stored in the storage device.

3. The method for determining a concentration according to claim 1, wherein the pressure drop characteristics are defined by the time required for a pressure indicated by the pressure sensor to drop to a specified pressure after changing the upstream valve to the closed state.

4. The method for determining a concentration according to claim 1, wherein the pressure drop characteristics are defined by the pressure reached after elapse of a specified time after changing the upstream valve to the closed state.

5. The method for determining a concentration according to claim 1, wherein the pressure drop characteristics are determined under conditions satisfying critical expansion conditions.

6. The method for determining a concentration according to claim 1, wherein the mixed gas contains a diluent gas and a source gas, and the concentration of the source gas is determined as the specified gas.

7. The method for determining a concentration according to claim 1, wherein the upstream valve is a control valve for adjusting the flow rate of the mixed gas.

8. A pressure-type flow rate control device comprising a restriction portion, an upstream valve provided upstream of the restriction portion, a pressure sensor for measuring a gas pressure between the restriction portion and the upstream valve, and a controller for receiving an output of the pressure sensor, the pressure-type flow rate control device being configured so that a mixed gas flows from the upstream side of the upstream valve,
wherein the controller determines pressure drop characteristics occurring after the upstream valve is changed from an open state to a closed state from output of the pressure sensor and determines a concentration of a specified gas in a mixed gas based on the pressure drop characteristics.

* * * * *